(12) United States Patent
Nadrag et al.

(10) Patent No.: US 9,761,341 B2
(45) Date of Patent: Sep. 12, 2017

(54) DEVICE TO IRRADIATE OBJECTS WITH ELECTROMAGNETIC RADIATION

(71) Applicant: SICO Technology GmbH, Bleiberg-Kreuth (AT)

(72) Inventors: Enrico Nadrag, Bad Bleiberg (AT); Christian Simcic, Latschach (AT)

(73) Assignee: SICO TECHNOLOGY GMBH, Bleiberg-Kreuth (AT)

( * ) Notice: Subject to any disclaimer, the term of this patent is extended or adjusted under 35 U.S.C. 154(b) by 0 days.

(21) Appl. No.: 15/040,189

(22) Filed: Feb. 10, 2016

(65) Prior Publication Data
US 2016/0240277 A1 Aug. 18, 2016

(30) Foreign Application Priority Data

Feb. 16, 2015 (AT) .................... A 78/2015

(51) Int. Cl.
*G21K 5/04* (2006.01)
*G21K 5/02* (2006.01)
*A61L 2/08* (2006.01)
*A61L 2/10* (2006.01)

(52) U.S. Cl.
CPC ............... *G21K 5/02* (2013.01); *A61L 2/08* (2013.01); *A61L 2/085* (2013.01); *A61L 2/10* (2013.01)

(58) Field of Classification Search
CPC ..................... G21L 5/00; G21K 5/02
USPC ... 250/492.1, 492.2, 492.21, 492.22, 492.23, 250/493.1, 494.1, 504 R
See application file for complete search history.

(56) References Cited

U.S. PATENT DOCUMENTS

| | | | |
|---|---|---|---|
| 2002/0049389 A1* | 4/2002 | Abreu | A61B 3/1241 600/558 |
| 2003/0021734 A1* | 1/2003 | Vann | B01J 19/0046 506/23 |
| 2011/0127448 A1 | 6/2011 | Ben-Shmuel | |
| 2013/0236353 A1 | 9/2013 | Blechschmidt et al. | |
| 2013/0270445 A1 | 10/2013 | Gaska et al. | |
| 2014/0117008 A1* | 5/2014 | Lautenschlaeger | H05B 6/6402 219/756 |

FOREIGN PATENT DOCUMENTS

| | | |
|---|---|---|
| EP | 0818206 | 1/1998 |
| EP | 2567713 | 3/2013 |
| KR | 2005-0119532 A | 12/2005 |
| WO | 2008/007908 A1 | 1/2008 |

OTHER PUBLICATIONS

Austrian Search Report, dated Sep. 10, 2015, from corresponding Austrian Application.
European Search Report dated Mar. 29, 2016; Application No. 16450001.9.

\* cited by examiner

*Primary Examiner* — Nicole Ippolito
(74) *Attorney, Agent, or Firm* — Young & Thompson

(57) ABSTRACT

A device (1) for irradiating titanium-dioxide-coated fibers with UV radiation includes a housing (2) that is filled with water. Bodies (4), including strips (5), which consist of quartz glass, are arranged in the housing (2). LEDs (7), which emit UV radiation, are paired with at least one of the longitudinal edges of the strips (5). UV radiation is uniformly emitted to the fibers by the strips (5), so that these fibers acquire anti-fouling properties.

20 Claims, 5 Drawing Sheets

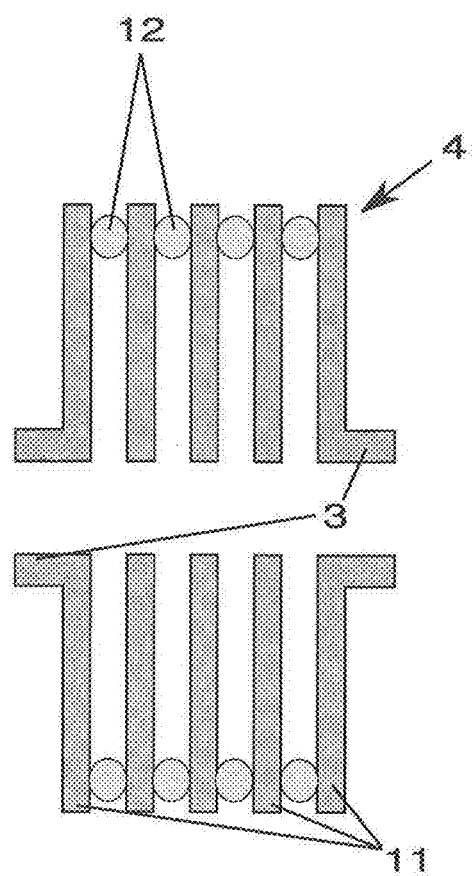

DEVICE TO IRRADIATE OBJECTS WITH ELECTROMAGNETIC RADIATION

FIELD OF THE INVENTION

The invention relates to a device for irradiating objects with electromagnetic radiation, such as, for example, electromagnetic radiation in the range of visible light, in the IR range, or in the UV range.

BACKGROUND OF THE INVENTION

For example, objects that are coated with titanium dioxide are irradiated with UV radiation in order to impart properties to the coating that consists of titanium dioxide, which can be present in particular in the form of particles in the nano-size range (=nanopowder), which properties prevent an undesirable buildup of solids ("fouling") on the surfaces of objects, in particular the accumulation ("growth") of sessile organisms. UV irradiation imparts "anti-fouling" properties to the objects that are coated with titanium dioxide.

A practical example is the irradiation of fibers, from which filter mats are produced for water desalination plants. In this case, it is to be achieved that during the shutdown of water desalination plants, no growth ("biofouling," "biofilm formation") develops on the filter mats, which consist of, for example, ceramic fibers coated with titanium oxide.

SUMMARY OF THE INVENTION

The object of the invention is to indicate a device with which the irradiation of any objects with electromagnetic radiation is possible with high effectiveness.

This object is achieved according to the invention with a device that has the features recited in the claims.

Preferred and advantageous embodiments of the device according to the invention are subjects of the subclaims.

In the case of the device according to the invention, the objects that are to be irradiated are exposed to the electromagnetic radiation after the radiation has passed through a wall that consists of material that is permeable to the radiation that is to be used (e.g., quartz for UV radiation, or silicon, in particular crystalline silicon, for IR radiation). Thus, in the case of the device according to the invention, a wall that acts as the radiation-distributing fiber optic light guide is provided between the object and the at least one source for the radiation. This wall can be designed as a tube, in which the object or the objects are accommodated and which is filled in particular with a liquid, such as water.

In the case of the device according to the invention, in an embodiment according to the invention, bodies that consist of material that is permeable to electromagnetic radiation in the area to be used (e.g., quartz glass for UV radiation, or silicon, in particular crystalline silicon, for IR radiation), are provided in the space in which the object to be irradiated or the objects to be irradiated are accommodated. Radiation sources are paired with the bodies. Thus, a uniform distribution of the radiation is produced in the space in which the objects are accommodated, so that the latter are struck uniformly by the radiation from all sides and, for example, the desired "anti-fouling" property of the objects is produced in particular by ceramic-based fibers that are coated with titanium dioxide.

The device according to the invention, however, also makes it possible to make the distribution of the radiation deliberately uneven so that areas of the object that require more radiation are more heavily irradiated.

In a preferred embodiment, the device has a housing that is shaped like, for example, a tube.

The bodies are preferably strips or plates that are oriented in the longitudinal direction of the (tubular) housing. The radiation sources are paired with, for example, the narrow sides of the strip-like bodies.

In a preferred embodiment, in particular strip-like bodies that project inward from the wall of the housing are provided.

In one embodiment, in particular strip-like bodies that are oriented pointing outward from the center of the housing are provided.

The radiation sources, which emit the electromagnetic radiation (visible light, IR radiation, or UV radiation), can be paired with the bodies that consist of clear material or can be accommodated in a recess (cavity) in the bodies that consist of material that is permeable to the radiation.

An embodiment of the invention is distinguished in that the outside surface of the wall, in particular the body of the device, which is irradiated with the electromagnetic radiation, is roughened. A roughening with peaks is quite especially preferred, so that the outside surfaces of the wall and the body are pointy and rough.

A preferred material of the wall and the body of the device according to the invention, with which at least one radiation source is paired, is quartz glass, which is suitable in particular when UV radiation, i.e., electromagnetic radiation in a non-visible range, is emitted as electromagnetic radiation. When IR radiation is used in the device according to the invention, a preferred material of the wall or the body of the device according to the invention, with which at least one radiation source is paired, is silicon, preferably crystalline silicon.

BRIEF DESCRIPTION OF THE DRAWINGS

Further details and features of the invention follow from the description below of preferred embodiments based on the drawings. Here:

FIG. 5 shows another embodiment of a device according to the invention in section.

DETAILED DESCRIPTION OF THE INVENTION

It is common to all embodiments that with the device according to the invention, the distribution of electromagnetic radiation is possible with high effectiveness in the visible and non-visible ranges in liquids. Thus, the device according to the invention makes it possible for tubes and fibers, hereinafter also hollow fibers, to irradiate uniformly and highly effectively with electromagnetic radiation in the visible and non-visible ranges (UV radiation or IR radiation).

Thanks to the special nature of the coupling of electromagnetic radiation in the visible and non-visible ranges in the wall that is used as a fiber optic light guide, which wall is designed, for example, in the form of at least one body that is used as a fiber optic light guide, which wall consists of material that is permeable to the selected radiation (quartz glass or silicon), which, when the wall is tubular, is filled with a liquid, e.g., water, or is arranged in such a liquid in the case of the body, the intended action of the device according to the invention is produced.

With all embodiments of the device according to the invention, it is possible to introduce electromagnetic radiation into the visible, infrared or ultraviolet range in a container that is filled with liquid in order to irradiate objects.

Preferred light sources are LEDs, but other light sources, which emit electromagnetic radiation in the desired wavelength range, can also be used.

In particular, the device according to the invention is suitable to emit electromagnetic radiation in the visible, infrared or ultraviolet range to a bundle of fiber-like objects, tubes, hair or other elongated objects and to apply them in a distributed manner uniformly or—if advantageous in an application—unevenly.

Figure 1:
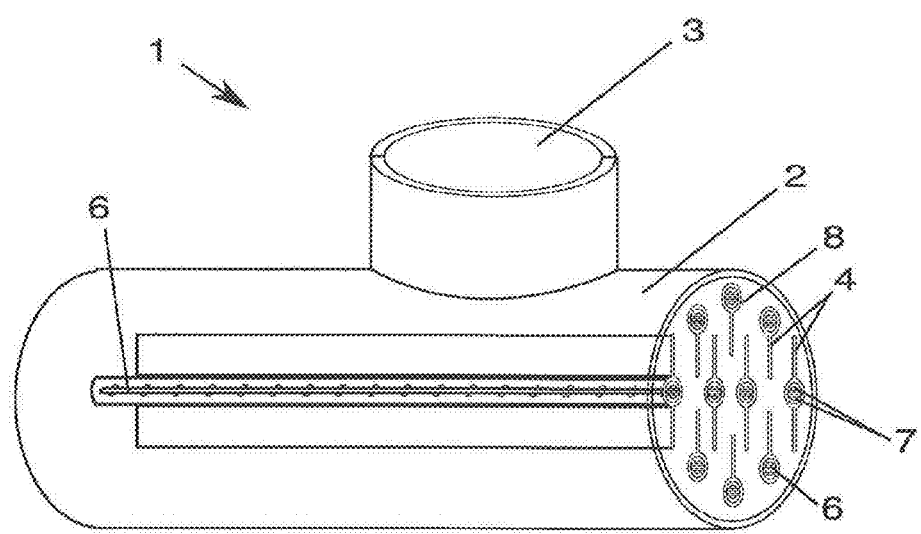
FIG. 1 shows a first embodiment of an arrangement according to the invention in an oblique view.

In the embodiment shown in FIG. 1, the device 1 comprises a tubular housing 2, on which in the embodiment shown in FIG. 1, a support 3 is provided as an inlet/outlet for liquid, in particular water. In the tubular housing 2, walls in the form of bodies 4 that distribute electromagnetic radiation, in particular light, infrared radiation or ultraviolet radiation, are provided. For purposes of better comprehensibility, an arrangement that consists of bodies 4 with their tubular areas 8, strips 5 and light sources 6 is depicted in a view in FIG. 1, although the housing 2 is in general not clear. The bodies 4 are designed as strips 5 that are oriented in the longitudinal direction of the tubular housing 2. A source 6 for electromagnetic radiation, for example in the form of LEDs 7, is paired with each strip 5.

In the embodiment shown in FIG. 1, the LEDs 7 are accommodated in a tubular area 8 of the body 4. The strips 5 project from area 8 in directions that are opposite to one another.

The strips 5 can project in different directions in a modified embodiment of the area 8 without being arranged opposite to one another. In this case, the LEDs 7 are accommodated back to back in the tubular areas 8.

In the bodies 4 provided in the edge area of the inside space of the tubular housing 2, strips 5 project only to one side of the tubular areas 8 of the bodies 4. The tubular areas 8 can also consist at least partially of a material that is permeable to the radiation that is used.

Figure 2:
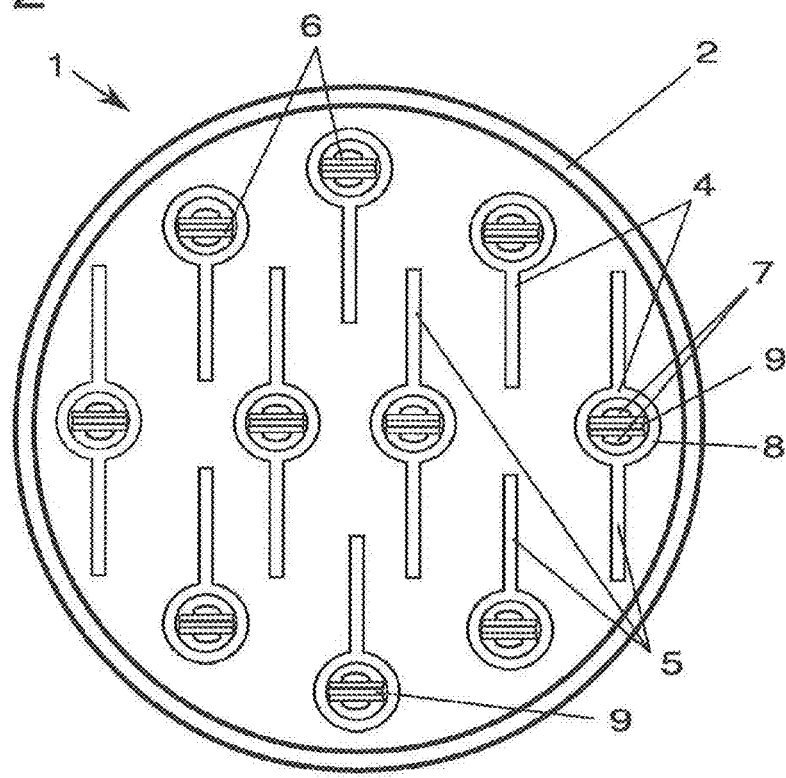
FIG. 2 shows a front view of the embodiment of FIG. 1.

Heat-dissipating elements 9 can be provided between the LEDs 7 (FIG. 2).

In the embodiment of the device 1 shown in FIGS. 1 and 2, the objects that are to be treated are arranged in the inside of the housing 2 between the bodies 4.

Figure 4:
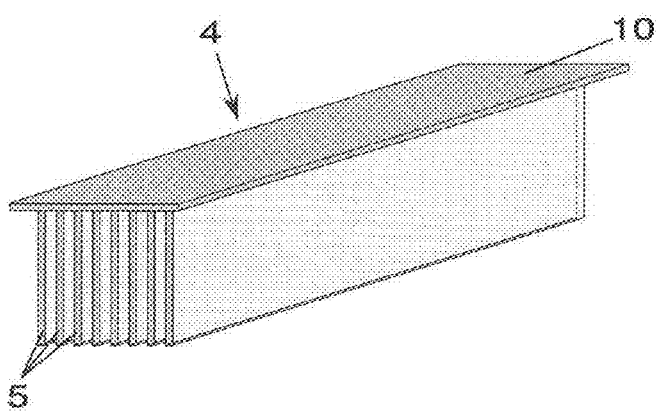
FIG. 4 shows the use of the device of FIG. 3.
Figure 3:
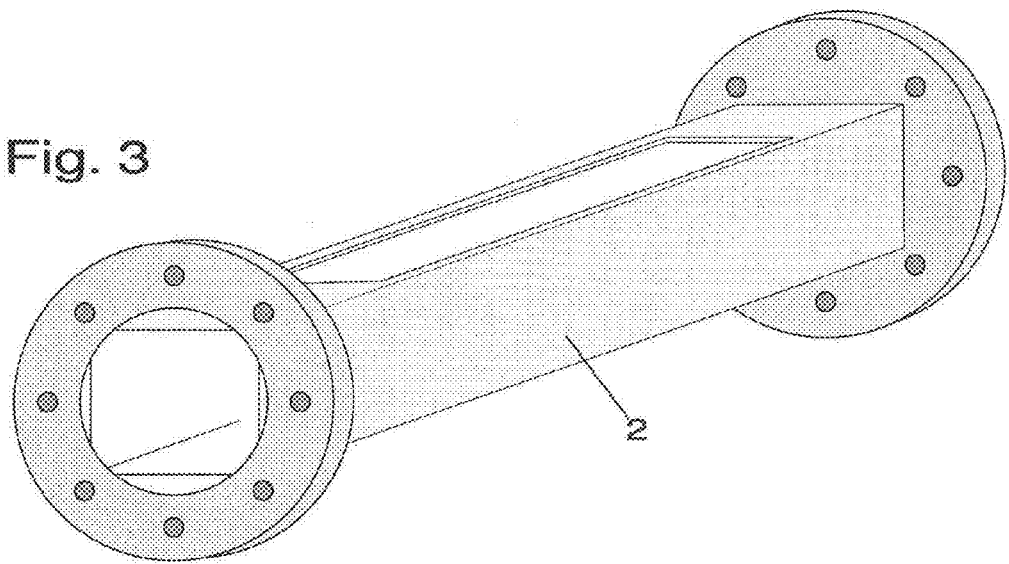
FIG. 3 shows another embodiment of a device according to the invention.

In the embodiment shown in FIGS. 3 and 4—in the unassembled state—a body 4, from which strips 5 project and into which electromagnetic radiation is coupled, is provided in the housing 2. In the body 4 of FIGS. 3 and 4, the strips 5 start from a common carrier 10, with which the radiation source(s) 6 is (are) paired.

Also, in the embodiment of device 1 shown in FIGS. 3 and 4, the objects that are to be treated are arranged inside the housing 2.

In the embodiment shown in FIG. 5, the wall forming the body 4 that distributes electromagnetic radiation is designed in the form of disks 11 that are connected together to form a packet, whereby sealing rings 12 (O-rings) are provided on the edge side between the disks. The electromagnetic radiation is coupled via the outside edge of the disks 11, distributed in particular over several points of the periphery of the disks 11.

The two outer disks 11 carry supports 3 as inlets and outlets. Lines for feeding and removing liquid (water) can be connected to the supports 3.

Figure 6:
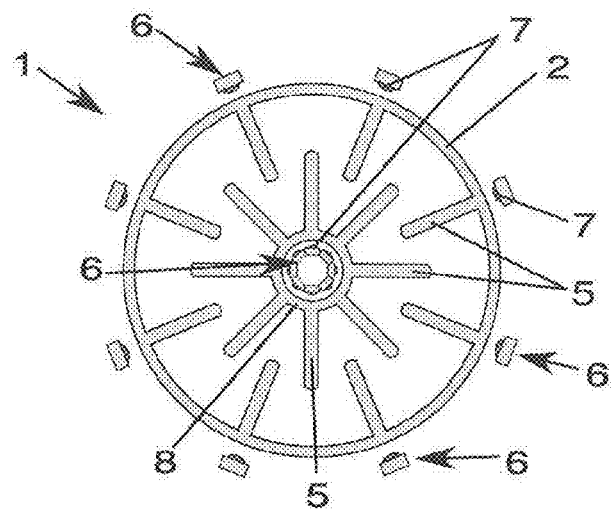
FIG. 6 shows another embodiment of a device according to the invention in front view.

The embodiment shown in front view in FIG. 6 comprises the tubular housing 2, from which strips 5 forming the wall project inward. In addition, strips 5 that project outward are provided from a tubular area 8 that forms the wall, which area is arranged coaxially to the housing 2. Both the strips 5 that project inward and those that project outward are radially oriented relative to the axis of the housing 2 in the embodiment of FIG. 6.

In the embodiment shown in FIG. 6, within the scope of the invention, the possibility exists of providing only the housing 2 with strips 5, or only the tubular area 8 with strips 5, or, as depicted in FIG. 6, both the housing 2 and the tubular area 8.

The strips 5 consist of, for example, quartz glass and can be integrally designed with the housing 2. LEDs 7 arranged outside of the housing 2 as sources 6 that emit electromagnetic radiation are paired with the strips 5 that project inward from the housing 2. In the inside of the tubular area 8, multiple LEDs 7 are arranged, of which in each case one is paired with the strips 5 that project outward from the tubular area 8.

The strips 5 have a width that is large so that the free end areas of the strips 5 that project from the outside to the inside and the strips 5 that project from the inside to the outside overlap one another.

The strips 5 that project inward from the housing 2 can be integrally designed with the housing 2. In this case, the housing 2 also consists of material that is permeable to the electromagnetic radiation that is emitted by the LEDs 7.

Figure 7:
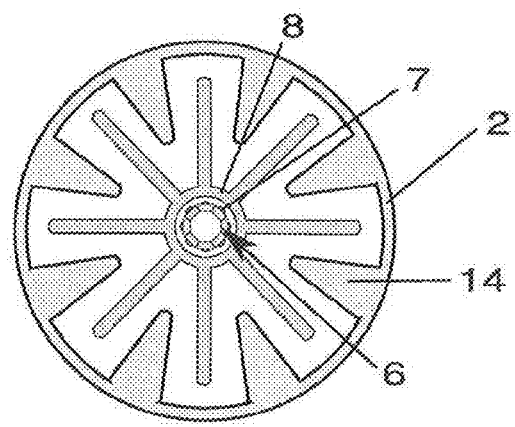
FIG. 7 shows another embodiment of a device according to the invention in front view.

In the embodiment shown in FIG. 7, projections 14 that project inward from the housing 2 and that are designed to be triangular in cross-section are provided. The projections 14 project between the strips 5, which project from the tubular area 8, in which LEDs 7 are provided.

In the embodiment shown in FIG. 7, the housing 2 and the projections 14 that are integral with it can be produced, for example, from a material other than quartz glass, e.g., from plastic or stainless steel.

In the embodiment shown in FIG. 7, LEDs 7 are provided only in the inside of the tubular area 8.

The strips 5 that project radially outward emit electromagnetic radiation, uniform in the embodiment, to the objects that are to be irradiated.

The projections 14 in particular have the purpose of attaching the in particular fiber-like objects (fiber bundles) to the strips 5.

Figure 8:
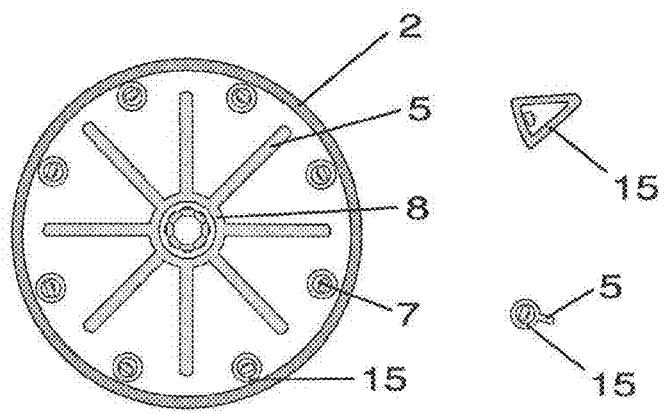
FIG. 8 shows another embodiment in front view with different variants of bodies.

In the embodiment shown in FIG. 8, the inside tubular area 8 is provided with strips 5 that point outward, as has been described based on FIGS. 6 and 7. On the inside of the jacket of the housing 2, bodies 4 are provided in the form of tubes 15, which are oriented parallel to the longitudinal axis of the housing 2 and in which LEDs 7 are accommodated. As shown in FIG. 8, the tubes 15, which are arranged on the inside of the jacket of the housing 2, can be paired with narrow strips 5 for distribution of electromagnetic radiation.

An alternative embodiment provides tubes 15 with, for example, triangular cross-sections, in which LEDs 7 are provided, instead of tubes 15 with circular cross-sections.

In all embodiments of the device 1 according to the invention, in which the radiation source, e.g., LEDs 7, is located inside, the housing 2 can consist of a material, such as plastic or stainless steel, which is not permeable to the electromagnetic radiation that is used.

In the case of outside radiation sources, for example LEDs 7, the housing 2 is made of a material that is permeable to the radiation that is to be used at least in the areas of the housing 2 through which radiation is to enter into the inside.

In the embodiments of a device 1 according to the invention shown in FIGS. 6 to 8, the objects that are to be treated with radiation are arranged inside the housing 2 between the strips 5.

Figure 9:
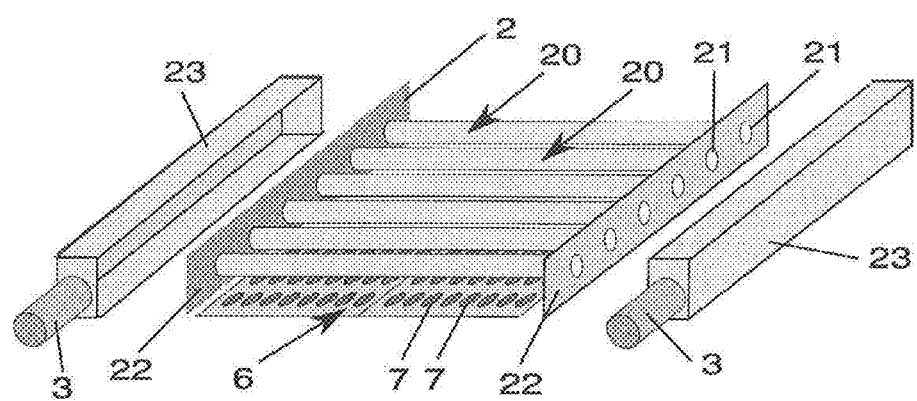
FIG. 9 shows another embodiment in an exploded view.

In the embodiment of a device 1 according to the invention shown in FIG. 9, the objects that are to be treated are arranged in the inside of walls 21 designed as tubes 20. The walls 21 in the form of tubes 20 are made from material that is permeable to the radiation that is to be used.

The tubes 20 are oriented parallel to one another and are connected on the end sides to plates 22 on whose outside are arranged chambers 23 (distributing chambers), which are equipped with supports 3 as inlets and outlets for a liquid (water). The plates 22, which bear the tubes 20, are tightly connected to the chambers 23, on which the supports are provided, so that a liquid, e.g., water, flows through a chamber 23, through the tubes 20, and into the other chamber 23.

Light sources 6 in the form of LEDs 7 are paired with the tubes 20 whose walls 21 are made from material that is permeable to the radiation that is to be used. Because of the provision that the electromagnetic radiation (e.g., light, UV light, IR radiation) that is emitted by the LEDs 7 does not directly strike the objects that are to be treated but rather only strikes through the walls 21 of the tubes 20 on the objects that are arranged in the tubes 20, the walls 21 of the tubes 20 act as fiber optic light guides, so that a uniform irradiation of the objects is achieved.

Figure 10:
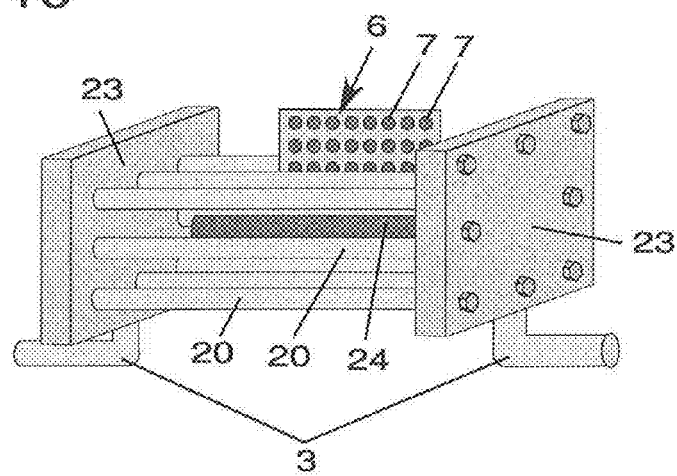
FIG. 10 shows another embodiment.

A modification of the embodiment of the device 1 according to the invention, shown in FIG. 9, is depicted in FIG. 10 in oblique view. Also here, tubes 20 are provided, whose walls 21 are made from material that is permeable to the radiation that is to be used. The tubes 20 are tightly connected by their ends to chambers 23 on which supports 3 are provided as inlets and outlets for a liquid, such as water. In the embodiment shown in FIG. 10, LEDs 7 and at least one radiation source 24 are paired with the tubes 20, whose walls 21 act as fiber optic light guides, as sources 6 for the electromagnetic radiation that is to be used, which radiation source 24 is surrounded on all sides by the tubes 20.

In summary, an embodiment of the invention can be described as follows:

A device 1 for irradiating titanium-dioxide-coated fibers with UV radiation comprises a housing 2, which is filled with water. Bodies 4, comprising strips 5, which consist of quartz glass, are arranged in the housing 2. LEDs 7, which emit UV radiation, are paired with at least one of the longitudinal edges of the strips 5. UV radiation is uniformly emitted to the fibers by the strips 5, so that these fibers acquire anti-fouling properties.

The invention claimed is:

1. A device (1) for irradiating objects, comprising:
a source (6) that emits electromagnetic radiation; and
a wall (21) that consists of material that is permeable to the electromagnetic radiation and is operable as a light guide for the electromagnetic radiation, the at least one wall located between objects to be irradiated, which are accommodated in a liquid, and the source (6) that emits the electromagnetic radiation.

2. The device according to claim 1, wherein the wall (21) forms a boundary surface of a tube in which the liquid and the objects to be irradiated are accommodated.

3. The device according to claim 1, further comprising:
a housing (2), having one or more of said walls (21) located therein in the form of bodies (4), the bodies formed of material that is permeable to the electromagnetic radiation that is emitted by the source (6),
wherein said source (6) is in the form of a plurality of sources (6) of the electromagnetic radiation, and
wherein each of the bodies (4) is paired with one of the plurality of said sources (6).

4. The device according to claim 3, wherein the bodies (4) comprise strips (5).

5. The device according to claim 4, wherein each of one said plurality of sources (6) is paired with an edge of a corresponding one of the strips (5).

6. The device according to claim 3,
wherein the housing (2) is tubular, and
wherein the bodies (4) each comprise one or more strips (5) that are radially oriented relative to the housing (2).

7. The device according to claim 6, wherein the strips (5) are oriented to extend in an outward direction from a center of the housing (2).

8. The device according to claim 7, wherein additional strips (5) are provided that are oriented pointing from the inside of the housing (2) inward toward a center of the housing.

9. The device according to claim 8, wherein the strips (5) that are oriented pointing outward overlap the additional strips pointing inward.

10. The device according to claim 6, wherein the strips (5) are oriented to extend from an inside of the housing (2) inward toward a center of the housing.

11. The device according to claim 10, wherein the strips (5) that point inward overlap other strips (5) inside the housing that are oriented pointing outward from the center of the housing (2).

12. The device according to claim 3, further comprising:
projections (14) that project from an inside of the housing (2).

13. The device according to claim 12, wherein the bodies (4) comprise strips (5) that project from the inside of the housing (2) to an outside the housing (2), and are arranged so that free edges of the strips (5) are located between said projections (14).

14. The device according to claim 3,
wherein the bodies (4) have tubular areas (8), and
wherein the bodies (4) further comprise strips (5) that project from said tubular areas (8).

15. The device according to claim 3, wherein said plurality of sources (6) are arranged outside of the housing (2).

16. The device according to claim 3, wherein said plurality of sources (6) are arranged in tubular areas (8) of the bodies (4) provided inside the housing (2).

17. The device according to claim 3, wherein the bodies (4) comprise strips (5) of tubular areas (8) of the bodies (4) that project to at least one side of the bodies (4).

18. The device according to claim 3, wherein the bodies (4) comprise tubes (15).

19. The device according to claim 3, wherein said plurality of sources (6) are arranged in tubes (15) provided on an inside of a jacket of the housing (2).

20. The device according to claim 1,
wherein the wall (21) consists of one of quartz glass or silicon, and
wherein the source (6) emits one of UV radiation or IR radiation.

* * * * *